United States Patent [19]

Margulies

[11] 4,381,779
[45] May 3, 1983

[54] DEFORMABLE SLIDABLE PISTON TO PROVIDE SELF-ASPIRATION IN HYPODERMIC CARTRIDGE AMPOULES

[75] Inventor: Herman Margulies, South Orange, N.J.

[73] Assignee: Sterling Drug Inc., New York, N.Y.

[21] Appl. No.: 284,055

[22] Filed: Jul. 16, 1981

[51] Int. Cl.³ .............................................. A61M 5/00
[52] U.S. Cl. .................................. 604/202; 604/232; 604/244; 604/900
[58] Field of Search ......... 128/218 R, 218 P, 218 PA, 128/218 D, 218 M, 215, 220, 261, 272, 234

[56] References Cited

U.S. PATENT DOCUMENTS

| | | | |
|---|---|---|---|
| 2,526,365 | 10/1950 | Jorgensen | 128/218 D |
| 3,224,445 | 12/1965 | Melott | |
| 3,295,525 | 1/1967 | Evers et al. | |
| 3,340,872 | 9/1967 | Cox | |
| 3,583,399 | 6/1971 | Ritsky | |
| 3,656,482 | 4/1972 | Sunnen | 128/261 |
| 3,662,753 | 5/1972 | Tassell | 128/218 M |
| 3,828,778 | 8/1974 | Weinhart | 128/261 |

FOREIGN PATENT DOCUMENTS

| | | | |
|---|---|---|---|
| 888863 | 12/1971 | Canada | 128/218 P |
| 1070785 | 12/1959 | Fed. Rep. of Germany | 128/218 P |

Primary Examiner—John D. Yasko
Attorney, Agent, or Firm—William G. Webb; B. Woodrow Wyatt

[57] ABSTRACT

The slidable piston closing the upper end of cartridge ampoules of the type used in hypodermic syringes is provided with a deformable section which, on forward and backward flexing, generates self-aspiration in the ampoule.

14 Claims, 6 Drawing Figures

DEFORMABLE SLIDABLE PISTON TO PROVIDE SELF-ASPIRATION IN HYPODERMIC CARTRIDGE AMPOULES

BACKGROUND OF THE INVENTION (a) Field of the Invention

This invention relates to slidable pistons which close the upper end of cartridge ampoules used in hypodermic syringes, the lower end thereof being closed by a pierceable diaphragm.

(b) Description of the Prior Art

In medical practice, hypodermic injections are sometimes administered subcutaneously, while others must be given intravenously, depending upon the particular medication to be administered. In either case, it is essential that the practitioner know with certainty, prior to injection of the medication, whether the hypodermic needle tip is located in a major blood vessel, such as a vein, or in subcutaneous tissue. Use of an aspirating syringe, in which a negative pressure can be generated in the syringe, affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly, or, if appropriate, the tip can be withdrawn and relocated.

Generally speaking, hypodermic syringes having aspirating capability belong to one of two classes, viz. manual aspirating and self-aspirating. In syringes of the former class, especially in those employing disposable, prefilled, medicament-containing ampoules, aspiration is effected by positively interengaging the syringe plunger rod with the slidable piston closing the upper end of the cartridge ampoule and slightly withdrawing the inter-engaged plunger/piston. There are many well known means of effecting such inter-engagement, the use of a barb or "harpoon" on the end of the plunger rod as disclosed by Mellott U.S. Pat. No. 3,224,445 being typical Syringes of the self-aspirating class usually require rather elaborate and expensive physical mechanisms which can be caused to induce a negative pressure in the syringe barrel or within a cartridge ampoule when the syringe is of a type adapted for use with disposable ampoules. One means of inducing aspirating conditions in syringes of the latter type is the method disclosed by Ritsky U.S. Pat. No. 3,583,399, in which a fixed stud surrounding the inner end of a double-ended hypodermic needle inside the barrel of the syringe impinges upon the flexible diaphragm which closes and seals the lower end of the cartridge ampoule. Thus downward pressure upon the ampoule causes inward flexing of the diaphragm. Release of the downward pressure on the ampoule causes return of the flexible diaphragm to its original planar configuration with concomitant generation of sufficient negative pressure within the cartridge ampoule to initiate aspirating action.

Another means of generating aspirating conditions in cartridge ampoules comprises use of a slidable piston having a deformable section on the lower end thereof. Deformation of the deformable section is produced by means of a plunger rod which extends through an interior cavity within the piston. Thus in Cox U.S. Pat. No. 3,340,872, the desired deformation is effected by means of a thin extension on the end of the plunger rod.

The same result can be obtained by use of a plunger-within-a-plunger assembly as described by Evers et al. U.S. Pat. No. 3,295,525 and Brown U.S. Pat. No. 3,834,387, the inner plunger, in effect, replacing, and serving the same purpose as, the thin plunger extension described by Cox.

In each of the Cox, Evers et al. and Brown syringes, downward pressure with the plunger against the deformable section and release thereof produces a slight negative pressure sufficient to generate aspirating conditions. However, each of the pistons described by Cox, Evers et al. and Brown has the disadvantage that the piston must be molded with an interior cavity which adds substantially to its cost. This is particularly true of the Cox piston, which, because part of the cavity has an expanded portion therein, captures the mold thus requiring special molding techniques.

BRIEF SUMMARY OF THE INVENTION

The slidable pistons provided by the present invention are of the type adapted to provide aspiration in an associated cartridge ampoule by the flexing of a deformable section of the piston. However, the deformable section of the pistons of this invention is contiguous with an exterior surface of the piston body, therefore eliminating the interior cavity. The pistons of this invention thus avoid the molding problems inherent in the prior art pistons having an interior cavity. The pistons of the present invention thus can be used with simple plungers which require no special mechanical means for interacting with the deformable section as in the Cox, Evers et al. and Brown syringes described above.

In order to fully describe the invention herein and the manner of using it, it will be necessary to use certain portions of a hypodermic syringe unit as points of reference to illustrate relative movements of parts of the syringe. Therefore, throughout this specification, and in the appended claims, the terms "lower" and "downwards" are intended to refer to the needle end of the syringe and its various associated parts as assembled or oriented in the syringe for injecting use. Conversely the terms "upper", "inner" or "upward" are intended to refer to the head end of the same.

The present invention is directed to slidable pistons for use in disposable cartridge ampoules which are sealed at the lower end thereof by a pierceable diaphragm and at the upper end thereof by a slidable piston and which contain an injectable fluid. The pistons are provided with a deformable section which is joined to, and is contiguous with, an exterior surface of the piston, whereby upon downward pressure on the piston and release thereof, the deformable section is caused to flex first forward and then backward to its original configuration thereby generating aspirating conditions in the cartridge ampoule

DETAILED DESCRITION OF THE INVENTION

The invention will now be described in detail with reference to the foregoing figures where like numerals are used to designate like parts.

Figure 1:
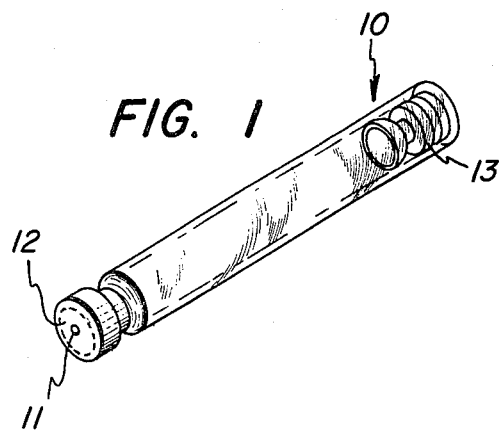
FIG. 1 is a perspective view of a cartridge ampoule equipped with a self-aspirating slidable piston according to the invention.

FIG. 1 illustrates a disposable cartridge ampoule, generally indicated by reference numeral 10, for use with hypodermic syringe holders, which consists of a cylindrical container, which can be glass or clear plastic, having a necked-down end and sealed at the necked-down end by a pierceable diaphragm 11 which is secured to the ampoule by a crimped on metal collar 12. As depicted in FIG. 1, the cartridge ampoule there illustrated is closed at its upper end by a piston 13, the subject of this invention, which is slidable within the bore of the ampoule.

Figure 2A:
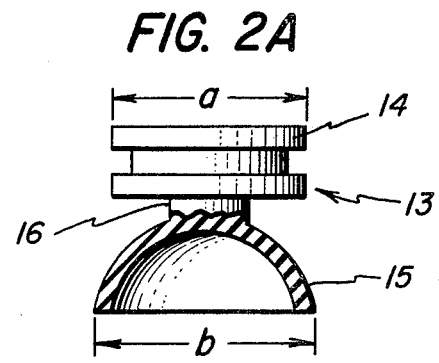
FIGS. 2A, 2B and 2C are elevational views in partial section showing three different embodiments of the self-aspirating pistons according to the invention.
Figure 2B:
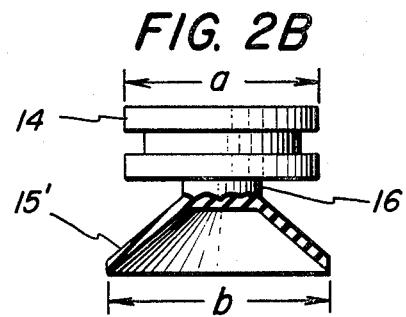
Figure 2C:
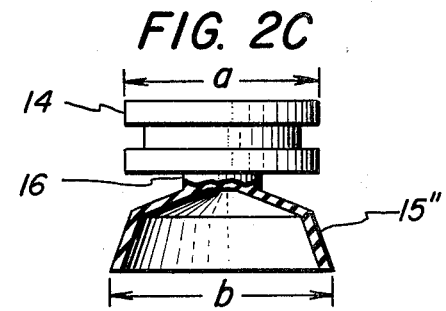

The structure of the self-aspirating piston of the invention is best understood by reference to FIGS. 2A, 2B, 2C and 2D, where the piston is, in each case, represented by general reference numeral 13. The piston consists of a rear body section 14 and a deformable section 15 connected to the rear body section by a neck portion 16 as shown in FIGS. 2A, 2B and 2C. The pistons of the invention are of unitary construction and can be fabricated either of natural rubber or synthetic rubbers, such as butyl rubbers, including brominated and chlorinated butyl rubbers, or neoprene or any flexible material which is capable of sterilization without causing deterioration of the piston and which is inert to the cartridge ampoule contents. The diameter (a) of the rear body section 14 is chosen so as to be slightly larger than the bore of the cartridge ampoule, in order to form a slidable frictional fit therein, and, for reasons to be further described hereinafter, the diameter (b) of the deformable section 15 is advantageously slightly larger than the diameter (a) of the rear body section.

The deformable section 15 is depicted in FIG. 2A as being generally hemispherical in shape. Such shape however is not essential to the self-aspirating action of the piston. It is only necessary that the deformable section be so-configured that it form a frictional seal with the inner wall of the cartridge ampoule and be capable of axial deformation upon exertion of downward pressure on the upper side of the piston and, on release of the downward pressure, return to its original configuration. Therefore alternatively, as depicted in FIGS. 2B and 2C, the deformable section can be either generally frustoconical (15') or frustoconical with an added bevel to the base of the frustoconical shape (15"), respectively.

Figure 2D:
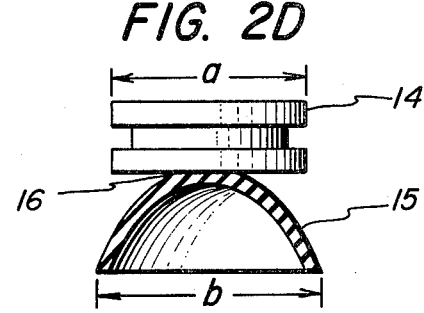
FIG. 2D is an elevational view in partial section of an alternative of the embodiment shown in FIG. 2A.

Moreover, it is not essential that the connecting neck portion 16 be elongated as shown in FIGS. 2A, 2B and 2C. Rather the rear body section 14 can be connected directly to the deformable section 15 as shown in FIG 2D.

Figure 3:
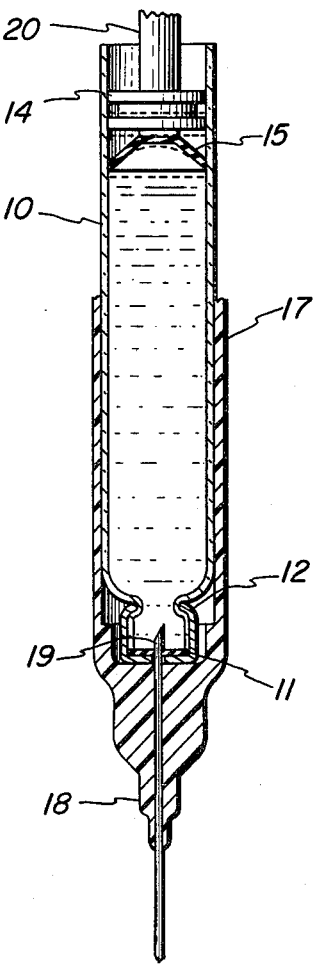
FIG. 3 is a longitudinal view in partial section showing the deformation of a self-aspirating slidable piston of the invention when the same is subjected to downward pressure by a syringe plunger rod and release thereof.

The method of generating self-aspiration with the slidable pistons of the invention is best understood by reference to FIG. 3 which shows a cartridge ampoule fitted with a self-aspirating slidable piston of the invention and the association of the cartridge ampoule with certain essential elements of a hypodermic syringe holder. Thus the ampoule 10 is held within the barrel 17 of a hypodermic syringe holder which is fitted, at its lower end, with a needle hub unit 18 and a double-ended hypodermic needle 19, the inner end of which extends inside the lower end of the syringe barrel where it pierces the diaphragm 11 which seals the lower end of the cartridge ampoule. With the needle thus in communication with the interior of the ampoule, the contents thereof can be expelled through the needle by downward pressure on a plunger rod 20. When the piston 13 is subjected to such downward pressure, the dome of the deformable section 15 of piston 13 will be slightly collapsed as indicated by the dotted lines in FIG. 3, and when the downward pressure is released, the memory of the flexible piston material will force return of the deformable section to its original configuration thus producing a slight negative pressure within the ampoule and thus an aspirating condition.

The aspirating effect is augmented by making the diameter (b) of the deformable section 15 greater than the diameter (a) of rear body section 14. The difference in the diameters of the two sections will have the effect of providing a frictional resistance differential between the rear body and the deformable sections with the result that the diminished frictional resistance in the body section, owing to its slightly smaller diameter, will promote return of the partially collapsed dome to its original configuration by allowing the rear body section to move backward more readily than the deformable section.

It will be understood that, although preferred embodiments have been described above in order to better illustrate the invention, alternative materials, forms and the like can be substituted for such aspects specifically described herein without either departing from the spirit of the invention or in any way adversely affecting the operability of the same.

Having thus described the invention and the advantages thereof, it is considered that the invention is to be broadly construed and limited only by the character of the following claims

I claim:

1. In a slidable piston for use in closing the upper end of a hypodermic syringe cartridge ampoule containing an injectable fluid therein and which is closed at its lower end by a pierceable diaphragm and at its upper end by a slidable piston, said piston being provided with a deformable section at the lower end thereof for generation of self-aspiration by deformation of said deformable section, the improvement which comprises:

a slidable piston having a rear body section connected to a deformable, generally dome shaped section by a neck portion, said deformable section being contiguous with an exterior surface of said piston, thereby obviating an interior cavity in said piston, said rear body section being of slightly lesser diameter than said deformable section and said rear body and deformable sections each being adapted for slidable frictional engagement with the bore of said cartridge ampoule whereby an aspirating condition is generated within said ampoule by the partial downward collapse of said dome and return thereof to its original shape upon alternate exertion of downward pressure on said piston and release thereof.

2. An improved slidable piston according to claim 1 wherein said deformable section is hemispherical in shape.

3. An improved slidable piston according to claim 1 wherein said deformable section is frustoconical in shape.

4. An improved slidable piston according to claim 1 wherein said deformable section is frustoconical with an added bevel at the base of said frustoconical shape.

5. An improved slidable piston according to claim 2 wherein said rear body section is connected directly to said deformable section.

6. An improved slidable piston according to claim 3 wherein said rear body section is connected directly to said deformable face section.

7. An improved slidable piston according to claim 4 wherein said rear body section is connected directly to said deformable face section.

8. In a cartridge ampoule for use in a hypodermic syringe, said ampoule containing an injectable fluid therein and being closed at its lower end by a pierceable diaphragm and at its upper end by a slidable piston, wherein said piston is provided with a deformable section at the lower end thereof for generation of self-aspiration by deformation of said deformable section, the improvement which comprises in combination:
   (A) a cartridge ampoule comprising a cylinder closed at its lower end by a pierceable diaphragm and closed at its upper end by
   (B) a slidable piston comprising a rear body section connected to a deformable, generally dome shaped section by a neck portion, said deformable section being contiguous with an exterior surface of said piston, thereby obviating an interior cavity in said piston, said rear body section having a slightly lesser diameter than said deformable section and said rear body and deformable sections each being adapted for slidable frictional engagement with the bore of said cartridge ampoule whereby an aspirating condition is generated within said ampoule by the partial downward collapse of said dome and return thereof to its original shape upon alternate exertion of downward pressure on said piston and release thereof.

9. A combination according to claim 8 wherein said deformable section is hemispherical in shape.

10. A combination according to claim 8 wherein said deformable section is frustoconical in shape.

11. A combination according to claim 8 wherein said deformable section is frustoconical with an added bevel at the base of said frustoconical shape.

12. A combination according to claim 9 wherein said rear body section is connected directly to said deformable section.

13. A combination according to claim 10 wherein said rear body section is connected directly to said deformable section.

14. A combination according to claim 11 wherein said rear body section is connected directly to said deformable face section.

* * * * *